US012636515B2

(12) United States Patent
Byers

(10) Patent No.: US 12,636,515 B2
(45) Date of Patent: May 26, 2026

(54) INTEGRATED, NONINVASIVE STIMULATION DELIVERY SYSTEM AND METHOD FOR TREATING ALZHEIMER'S DISEASE SYMPTOMS

(71) Applicant: Andrea Byers, Bristow, OK (US)

(72) Inventor: Andrea Byers, Bristow, OK (US)

( * ) Notice: Subject to any disclaimer, the term of this patent is extended or adjusted under 35 U.S.C. 154(b) by 480 days.

(21) Appl. No.: 18/319,082

(22) Filed: May 17, 2023

(65) Prior Publication Data

US 2023/0405353 A1      Dec. 21, 2023

Related U.S. Application Data

(60) Provisional application No. 63/342,700, filed on May 17, 2022.

(51) Int. Cl.
| | |
|---|---|
| *A61N 5/06* | (2006.01) |
| *A61H 9/00* | (2006.01) |
| *A61H 21/00* | (2006.01) |
| *A61H 23/02* | (2006.01) |

(52) U.S. Cl.
CPC ......... *A61N 5/0622* (2013.01); *A61H 9/0092* (2013.01); *A61H 21/00* (2013.01); *A61H 23/02* (2013.01); *A61H 2201/10* (2013.01); *A61H 2201/123* (2013.01); *A61H 2201/1607* (2013.01); *A61H 2201/1611* (2013.01); *A61H 2201/165* (2013.01); *A61H 2205/026* (2013.01); *A61H 2205/04* (2013.01); *A61H 2209/00* (2013.01); *A61N 2005/0606* (2013.01)

(58) Field of Classification Search
CPC ........ A61H 9/00; A61H 9/005; A61H 9/0007; A61H 9/0092; A61N 5/0603
See application file for complete search history.

(56) References Cited

U.S. PATENT DOCUMENTS

| | | | |
|---|---|---|---|
| 10,111,729 B1 | 10/2018 | Lowe et al. | |
| 2006/0161200 A1* | 7/2006 | Fallah .................. | A61H 9/0078 |
| | | | 606/204.15 |
| 2007/0038206 A1 | 2/2007 | Altshuler et al. | |
| 2009/0216178 A1* | 8/2009 | Lee .......................... | A61N 7/00 |
| | | | 604/22 |
| 2009/0216219 A1 | 8/2009 | Venter et al. | |

(Continued)

OTHER PUBLICATIONS

International Search Report and Written Opinion in PCT/US2023/067110 dated Nov. 16, 2023.

*Primary Examiner* — Justine R Yu
*Assistant Examiner* — Christopher E Miller
(74) *Attorney, Agent, or Firm* — Crowe & Dunlevy, P.C.

(57) ABSTRACT

Disclosed herein is a method of treating neurodegenerative diseases involving accumulation of abnormal proteins in the central nervous system (CNS) of a user. The method includes utilizing an intraoral device to apply photobiomodulation and vibration to specific points on hard and soft palates of the user to stimulate the user's glymphatic system and decongest hyperphosphorylated tau and amyloid proteins and toxins, and simultaneously with the utilization of the intraoral device, applying a transcranial device to exert vasopneumatic compression and photobiomodulation on the user's head and neck to stimulate the user's lymphatic system and enhance the flow of lymphatic fluid towards the subclavian lymphatic pathway.

13 Claims, 7 Drawing Sheets

(56)　　　　　　References Cited

U.S. PATENT DOCUMENTS

| | | | |
|---|---|---|---|
| 2013/0131558 A1* | 5/2013 | Lee | A61H 21/00 |
| | | | 601/2 |
| 2016/0158544 A1* | 6/2016 | Guarraia | A61N 1/0551 |
| | | | 607/2 |
| 2017/0095396 A1* | 4/2017 | Chase | A61F 5/3707 |
| 2019/0262212 A1* | 8/2019 | Schroeder | A61H 1/0296 |
| 2021/0205634 A1* | 7/2021 | Sverdlov | A61N 5/0622 |
| 2021/0290971 A1* | 9/2021 | Cockrell | A61N 5/0603 |
| 2022/0040492 A1 | 2/2022 | Arendash | |
| 2022/0054828 A1* | 2/2022 | Biswas | A61B 5/682 |
| 2022/0054856 A1* | 2/2022 | Wang | A61N 1/36025 |
| 2022/0118274 A1* | 4/2022 | Brawn | A61C 7/08 |
| 2022/0323784 A1* | 10/2022 | Cassano | A61N 5/0618 |
| 2023/0320925 A1* | 10/2023 | Smith | A61M 16/0683 |
| | | | 601/134 |

* cited by examiner

INTEGRATED, NONINVASIVE STIMULATION DELIVERY SYSTEM AND METHOD FOR TREATING ALZHEIMER'S DISEASE SYMPTOMS

CROSS-REFERENCE TO RELATED APPLICATIONS

This application claims the benefit of U.S. Provisional Application No. 63/342,700, filed on May 17, 2022, and incorporates said provisional application by reference in its entirety into this document as if fully set out at this point.

BACKGROUND OF THE INVENTION

1. Field of the Invention

The invention disclosed herein is directed to an integrated, noninvasive stimulation delivery system and method for treating Alzheimer's disease. The inventive system and method integrate noninvasive stimulation delivery technologies, e.g., vasopneumatic compression, photobiomodulation, and vibration, to synergistically stimulate glymphatic flow to consistently clear toxins from a patient's brain with mild-to-moderate dementia and Alzheimer's disease.

2. Description of the Related Art

Aging is a major risk factor for many neurological disorders, including Alzheimer's disease (AD). Although Alzheimer's is not normal aging, age is the biggest risk factor for the disease. According to the Alzheimer's Association of America, the U.S. population aged 65 and over is expected to double by 2030. Due to projected increases in AD diagnoses in the U.S., the estimated cost to third-party pay systems will increase to $20 trillion over the next 40 years. Another primary concern for these costs is that Alzheimer's makes treating other diseases more expensive, as most individuals with AD have one or more comorbidities that complicate the management of the condition and increase costs.

With Alzheimer's, it isn't just those with the disease who endure the devastating consequences of the disease with declining memory, cognition, and reduced quality of life. AD also significantly impacts the caregivers and families. Caring for an individual with Alzheimer's takes longer, lasts longer, is more personal and invasive, and takes a heavy toll on the caregiver's health. More than 60% of Alzheimer's caregivers rate the emotional stress of caregiving as high or very high, with one-third reporting symptoms of depression. Consequently, caregivers may have negative impacts on their own health, employment, income, and family finances, considering the physical and emotional toll of caregiving.

The mechanisms behind brain waste clearance from the parenchyma through meninges and vessels with molecular markers (e.g., endothelial cells of conventional lymphatic vessels) play a paramount role in cerebrospinal fluid (CSF) drainage. These mechanisms can successfully clear macromolecules and immune cells from the subarachnoid space into the cervical lymph nodes. Since these vessels do not reach the parenchyma, complementary mechanisms are required. In that regard, the brain has another clearance mechanism in which interstitial solute transport across the blood-brain barrier (BBB) drains into the bloodstream. However, this route can be hindered by the large distances between interstitial solutes and the BBB. Moreover, the tightly sealed endothelium of brain capillaries precludes normal systemic interstitial and lymphatic flow into the brain. To bypass this situation, other clearance routes are favored by the body, such as CSF-interstitial fluid (ISF) bulk flow of the glymphatic system.

A breakdown in CSF-ISF exchange occurs in Alzheimer's disease and other neurological conditions. Alzheimer's is the most common type (60-70% of total) of dementia and is mainly characterized by hyperphosphorylated tau and amyloid-$\beta$ (A$\beta$) protein deposition, wherein an imbalance between A$\beta$ production and clearance results in toxic accumulation (FIG. 1). One factor influencing CSF movement is arterial pulsatility and movement of vessel walls caused by the cardiac cycle. Arteries, when pulsating, momentarily increase pressure on the surrounding fluid, extravasating the perivascular space. The positive pressure of CSF production drives its movement from the choroid plexus and is supported by the activity of cilia and the process of deep respiration. Astrocytes allow fluid movement between perivascular spaces and the interstitium via water channels (AQP4, FIG. 2).

The pathway for CSF fluid drainage occurring between the arachnoid and the pia matter of the meninges can drain into the bloodstream through the arachnoid granulations located along the superior sagittal sinus and the transverse sinuses. Alternatively, CSF fluid drainage can reach the lymphatic vasculature of the nasal mucosa by crossing the cribriform plate, localized under the olfactory bulbs, along the olfactory nerves. The meningeal lymphatics enable the drainage of macromolecules and immune cells (FIG. 2). While the CSF fluid drains back to the bloodstream, the macromolecules and immune cells localized within the CSF drain primarily through the meningeal lymphatic vessels to reach the deep cervical lymph nodes.

The glymphatic system is a concept associated with CSF and ISF dynamics within the CNS (FIG. 3). The term glymphatic is derived from glial and lymphatic systems. The glymphatic system does not represent the discovery of a previously unknown anatomical structure but rather a brain-wide paravascular pathway from CSF and ISF exchange that facilitates the efficient clearance of macromolecules and waste from the brain (FIG. 3). In AD, A$\beta$ congestion is both a symptom and disease indicator. Specifically, individuals with AD have impaired perivascular circulation, which inhibits A$\beta$ from readily being removed. In addition, aging has been associated with peripheral lymphatic dysfunction affecting T cell egress and macromolecule drainage. In peripheral tissues, circulating ISF is recycled into the local lymphatic system, thereby cleaning tissues and preventing the accumulation of potentially toxic compounds, such as cellular metabolites or debris from damaged or necrotic cells.

A major risk factor for many neurological pathologies, such as Alzheimer's, poses a global health challenge associated with declining memory, cognition, and reduced quality of life. Current medications and treatments for treating Alzheimer's disease symptoms display notable side effects, including nausea, vomiting, constipation, dizziness, impaired alertness, impaired motor coordination, worsening depression, suicide ideation, sleep paralysis, and compromised respiratory function. Recent findings show that meningeal and cranial nerve glymphatic decongestion may affect the removal of the tau and A$\beta$ protein plaques from the central nervous system (CNS). The glymphatic system, i.e., aquaporin 4 (AQP4)-facilitated exchange of cerebrospinal fluid (CSF) with interstitial fluid (ISF), may provide a promising clearance pathway for these diseases; however, a significant obstacle to treating these diseases is connecting the new glymphatic flow physiological science to affordable, applicable daily modalities for individuals with Alzheimer's disease. These modalities effectively remove glymphatic congestions, such as accumulated amyloid proteins, a major contributing factor to the progression of this neurological condition.

Currently, studies are underway to test techniques and effectiveness in clearing Aβ and tau from the central nervous system. One such technique is photobiomodulation (PBM), which is a dual-modality method for treating neurodegenerative diseases. PBM is gaining attention as a safe, antiviral, and anti-inflammatory approach to treat neurodegeneration with photons, stimulate mitochondrial increases in ATP and proteasomes, and aid in misfolded protein removal. PBM alters multiple genes' expression and upregulates multiple pathogenic pathway inflammation, reactive oxidative stress, mitochondrial disorders, insulin resistance, epigenetic defects, regulation of neuroprotective factors, and regional hypoperfusion in the brain.

Only minimal manual neurolymphatic drainage has been attempted by trained and certified skilled therapists that can provide such glymphatic and lymphatic decongestion. These skilled individuals can be costly, and their availability is sparse. Therefore, it is desirable to provide an improved system and method for treating Alzheimer's disease that will decrease the burden on healthcare systems and caregivers while also improving daily life for sufferers of cognitive impairments, including alleviating dependence on others.

Before proceeding to a brief summary and subsequent detailed description of the invention, however, it should be noted and remembered that the description of the invention which follows, together with the accompanying drawings, should not be construed as limiting the invention to the examples (or embodiments) shown and described. Those skilled in the art to which the invention pertains will be able to devise other forms of this invention within the ambit of the appended claims.

BRIEF SUMMARY OF THE INVENTION

The invention disclosed herein provides an integrated, noninvasive stimulation delivery system and method for treating Alzheimer's disease, and more particularly, a system and method that integrate noninvasive stimulation delivery technologies, e.g., vasopneumatic compression, photobiomodulation, and vibration, to synergistically stimulate glymphatic flow to consistently clear toxins from a patient's brain with mild-to-moderate dementia and Alzheimer's disease.

It is further desirable to provide a system and method that sequentially integrate photobiomodulation with vibration in an intraoral device to stimulate glymphatic pathway clearance of toxins toward the cranial nerve pathway and into the systemic lymphatic pathway and with a vasopneumatic transcranial device to stimulate lymphatic flow at the cranial nerve exit of the skull in order to decrease tau and Aβ, consequently increasing cognition and independence, in daily living activities, in individuals with Alzheimer's disease.

In general, the invention enhances glymphatic decongestion and lymphatic efflux by combining photobiomodulation and vibration techniques in intraoral and transcranial devices. The transcranial device utilizes vasopneumatic compression and photobiomodulation to stimulate cervical lymphatic flow and transcranial lymphatic flow. The two-device system is used in tandem to remove tau and amyloid proteins from the CNS. The transcranial device opens a superficial pathway for removing toxins and proteins from perivascular spaces to maintain the homeostasis of protein and lymph through transcranial lymphatic channels. The inventive system and method apply vasopneumatic transcranial pressures to route lymphatic fluid toward the subclavian lymphatic pathway for effective and efficient lymphatic congestion clearing.

The intraoral device eliminates the need for a trained health care provider to administer the intraoral protocol while ensuring continuous treatment delivery through vibration and photobiomodulation of seventeen stimulation points on the hard and soft palate. The intracranial device decongests brain tau and amyloid proteins and toxins towards the superficial lymphatic pathway through the cranial nerves. Perivascular lymphatic drainage from the glymphatic and meningeal pathways prohibits the buildup of tau and amyloid peptides, maintains homeostasis of the cerebrospinal fluid, and averts cognitive decline in Alzheimer's disease. The glymphatic network serves as the initial waste clearance for proteins and metabolic products via connection to the authentic lymphatic network associated with the dura covering of the brain and cranial nerves and large vessels at the skull exits. Virchow-Robin Spaces and the Arachnoidal Septi, along the olfactory and optical nerves, transport intracranial lymphatic load towards the subclavian lymph nodes through cervical lymph pathways; this flow is enhanced through manual intraoral drainage procedures.

Removal of hyperphosphorylated tau and amyloid-beta from the brain improves cognition and functional activities of daily living, as well as overall independence. The noninvasive devices disclosed herein stimulate glymphatic flow, have shown no side effects, and are easily tolerated in everyday use. Stimulating glymphatic and transcranial flow enhances protein clearance from the CNS to benefit daily functional outcomes.

The invention disclosed herein provides an innovative treatment modality by combining a transcranial device and an intraoral device to remove toxins from the CNS. These devices remove hyperphosphorylated tau and amyloid beta from brains of individuals over age 65, with mild-to-moderate cognitive impairment, evidenced by baseline blood work, using blood testing for hyperphosphorylated tau, amyloid beta-40, (Aβ40, Aβ42), Apolipoprotein E prototype, Amyloid Probability Score (APS, calculated from plasma Aβ42/40 ratios), and participant age. This is coupled with the Saint Louis Mental Status Examination (SLUMS) score at baseline and at 90 days. Daily treatments with these two devices stimulate the removal of Aβ from the CNS.

The foregoing has outlined in broad terms some of the more important features of the invention disclosed herein so that the detailed description that follows may be more clearly understood. The invention is not limited in its application to the details of the construction and to the arrangements of the components set forth in the following description or illustrated in the drawings. Instead, the invention is capable of other embodiments and of being practiced and carried out in various other ways not specifically enumerated herein. Finally, it should be understood that the phraseology and terminology employed herein are for the purpose of description and should not be regarded as limiting unless the specification specifically so limits the invention.

BRIEF DESCRIPTION OF THE DRAWINGS

These and further aspects of the invention are described in detail in the following examples and accompanying drawings.

DETAILED DESCRIPTION OF THE INVENTION

Figure 1:
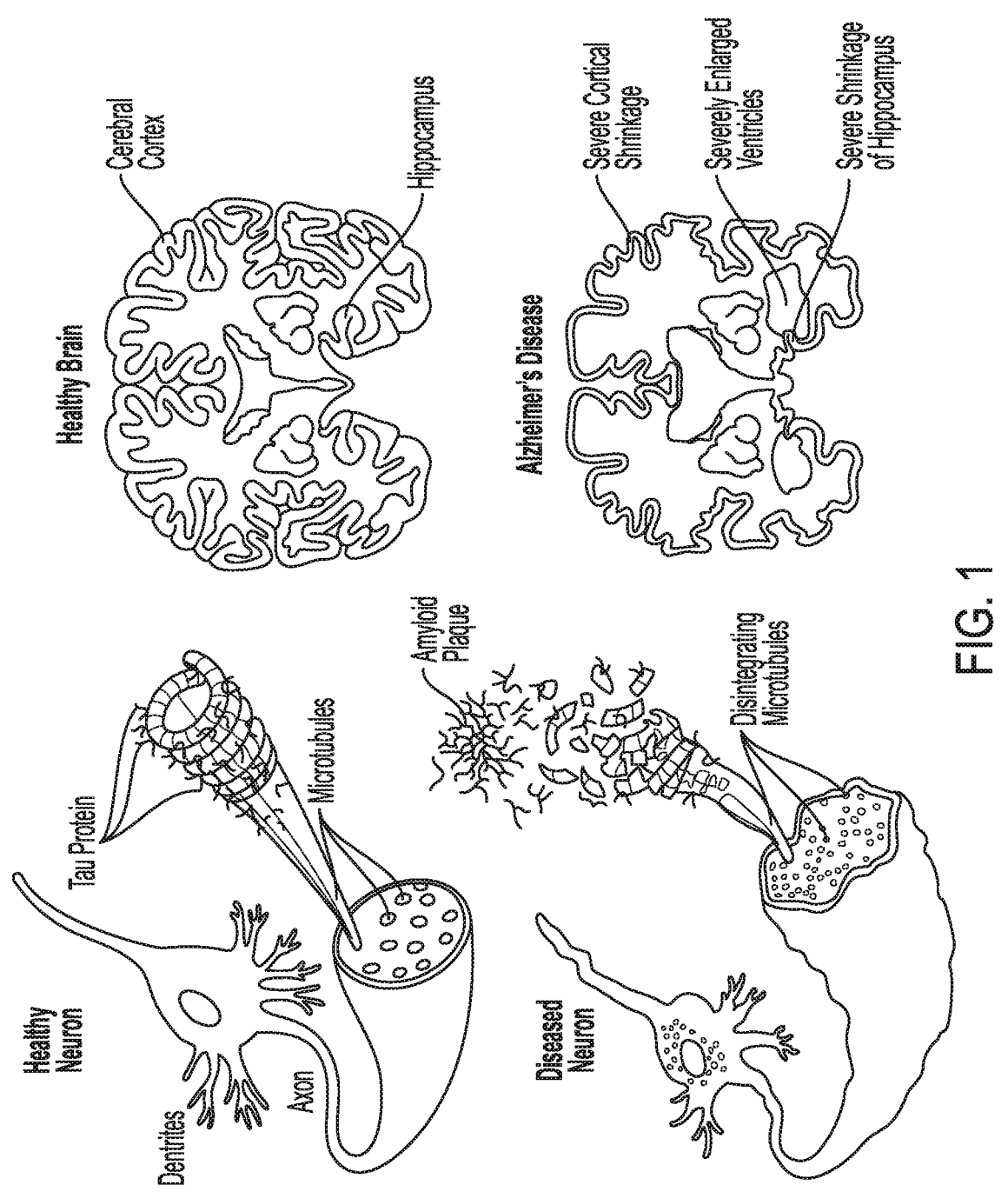
FIG. 1 illustrates amyloid plaque formation and brain pathology in Alzheimer's disease.
Figure 2:
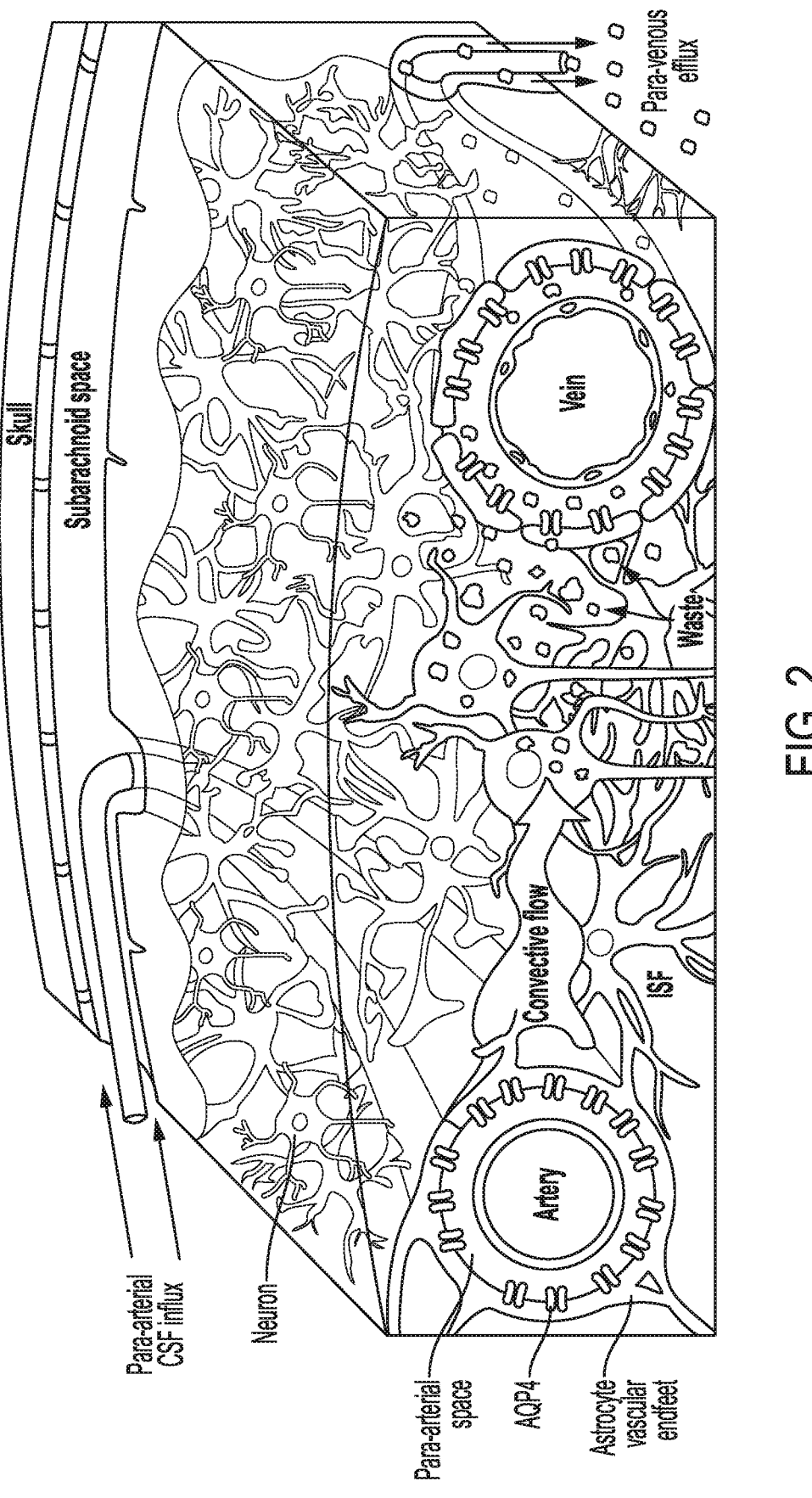
FIG. 2 illustrates the glymphatic system.
Figure 3:
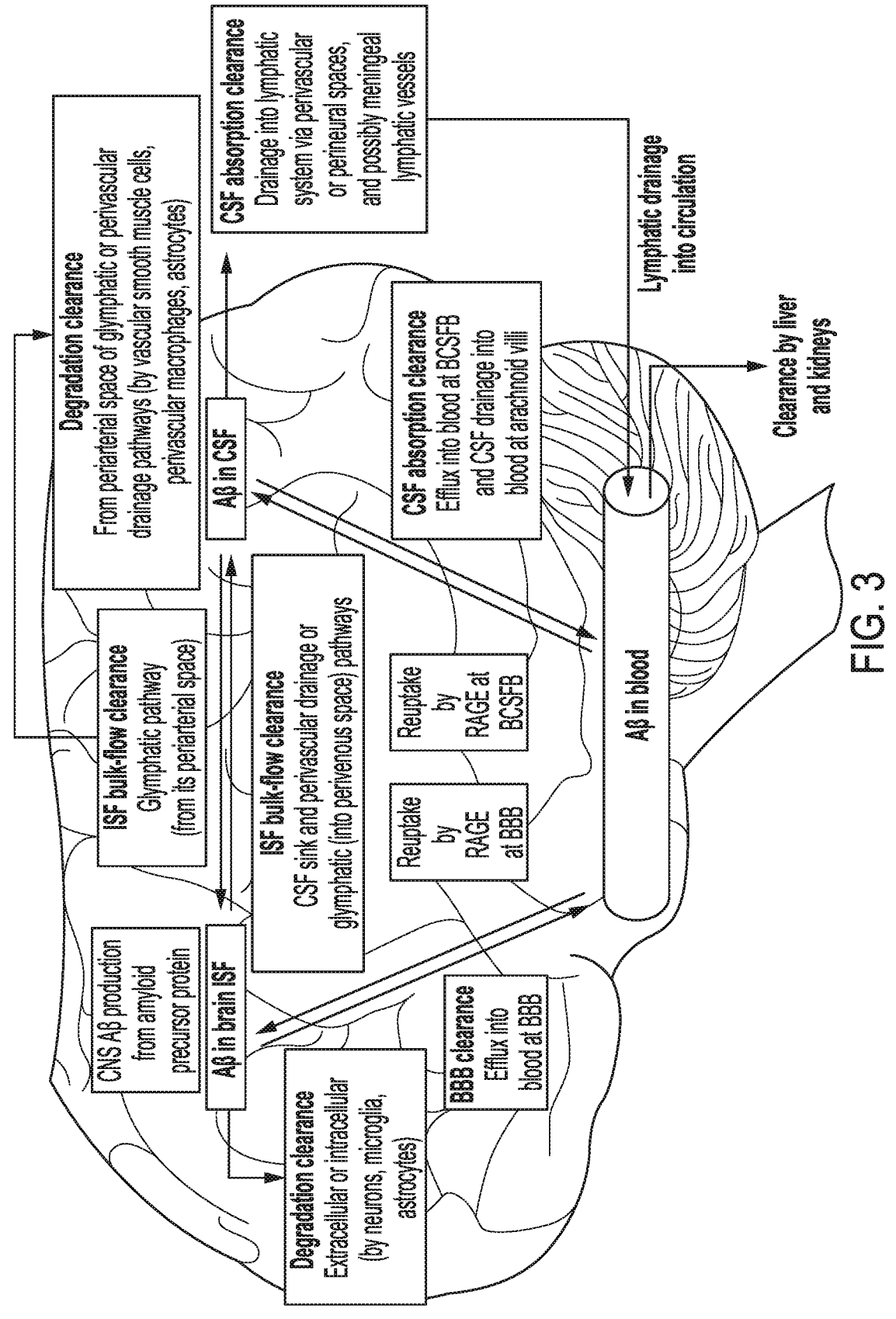
FIG. 3 illustrates the clearance of Aβ by degradation and absorption into the cerebrospinal fluid and interstitial fluid to/from the bloodstream.

While this invention is susceptible of embodiment in different forms, there are shown in the drawings and will herein be described hereinafter in detail some specific embodiments of the invention. However, it should be understood that the present disclosure is to be considered an exemplification of the principles of the invention and is not intended to limit the invention to the specific embodiments so described.

The invention is concerned with an innovative treatment strategy that involves the synergistic use of a transcranial device and an intraoral device, specifically designed to aid in the clearance of macromolecules, including but not limited to amyloid-beta (Aβ) and tau proteins, from the Central Nervous System (CNS) in individuals experiencing mild-to-moderate cognitive impairment as a result of Alzheimer's disease. This unique approach seeks to alleviate glymphatic congestion by stimulating meningeal decongestion, effectively rerouting these macromolecules towards cranial nerve lymphatic pathways for subsequent removal from the CNS.

Figure 4:
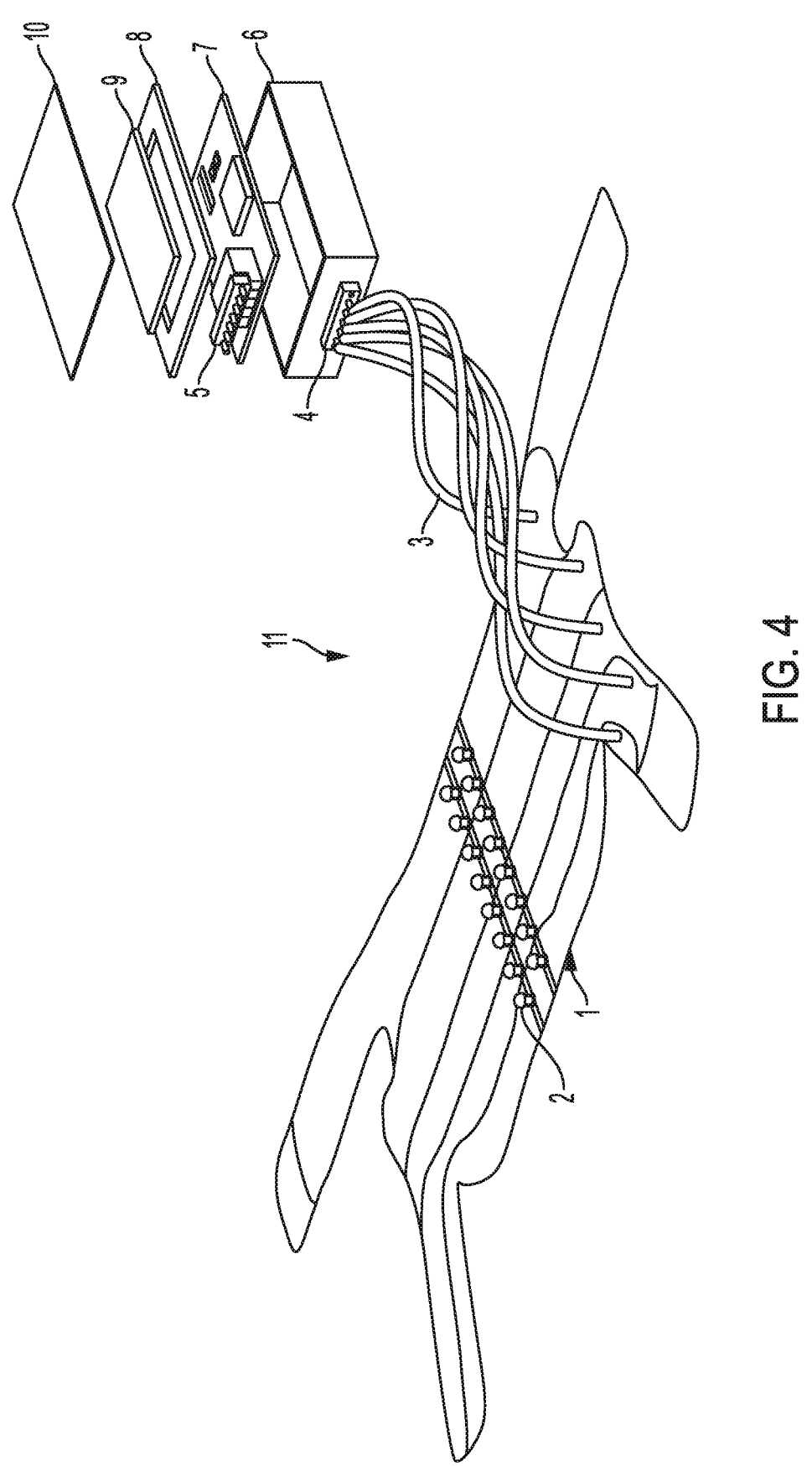
FIG. 4 is an exploded, perspective view of an example of a transcranial sequential vasopneumatic device configured to pulse 810 nm near-infrared light in accordance with an illustrative embodiment of the invention disclosed herein.
Figure 5:
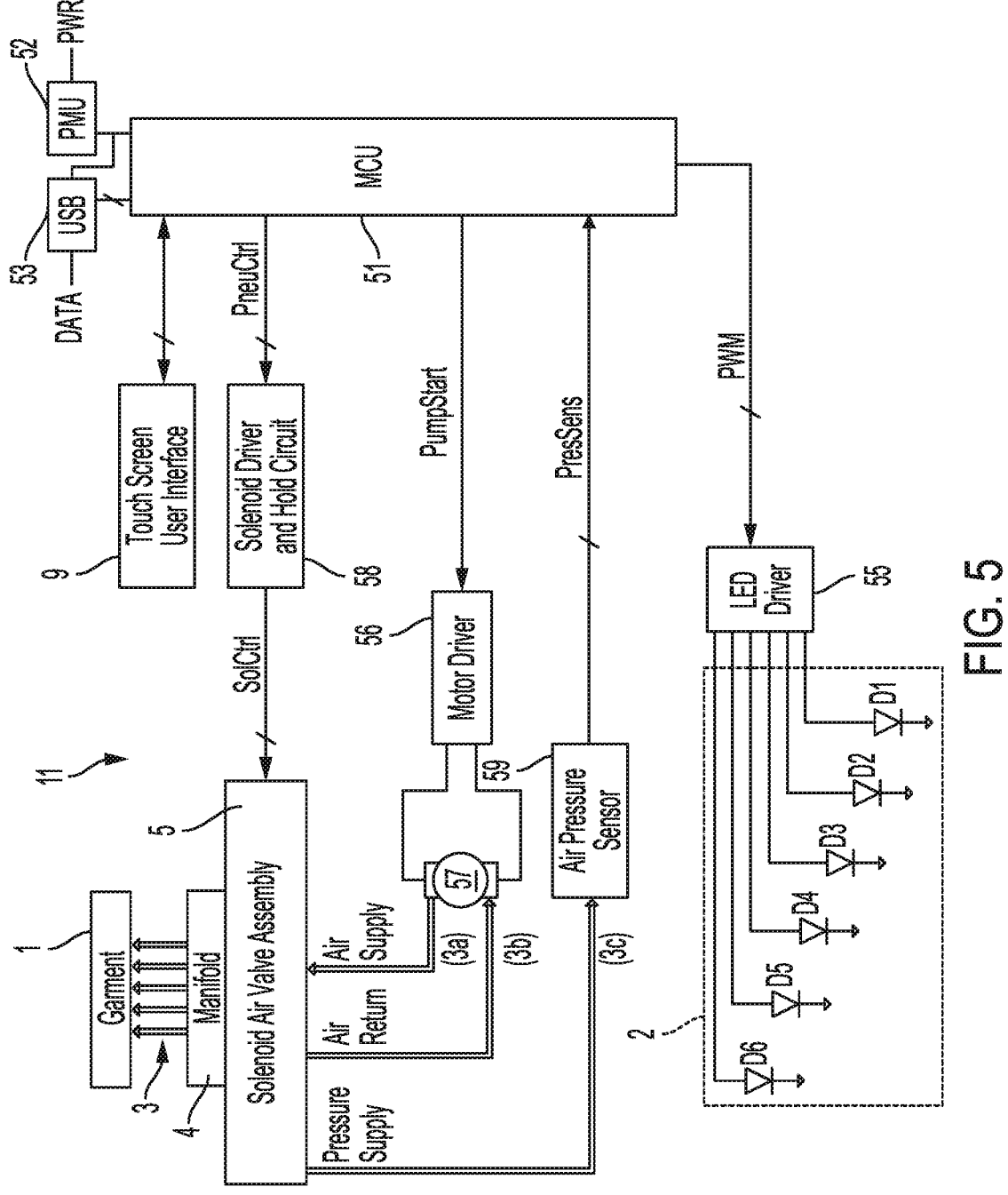
FIG. 5 is an electrical schematic of an example of a transcranial sequential vasopneumatic device in accordance with an illustrative embodiment of the invention disclosed herein.
Figure 6:
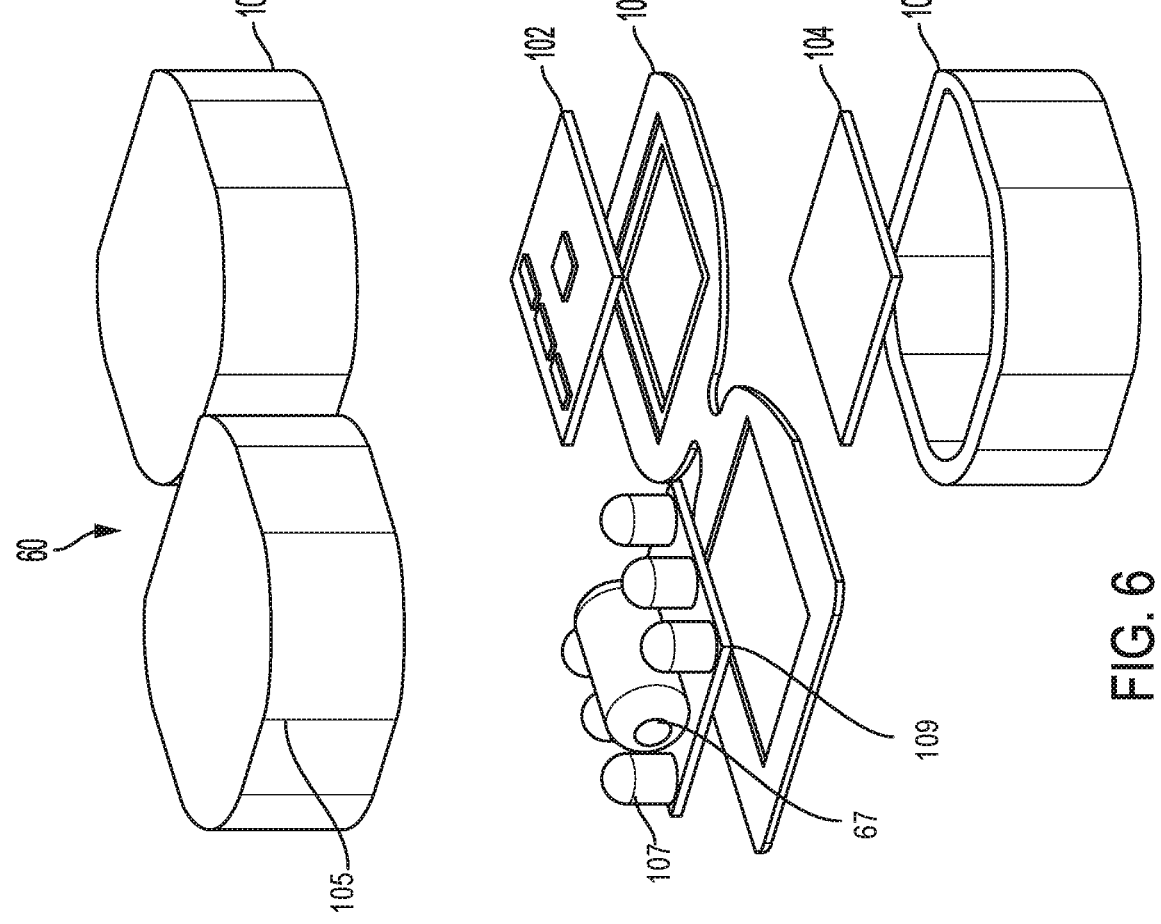
FIG. 6 is an exploded, perspective view of an example of an intraoral device configured to emit 670 nm near-infrared light and provide vibration stimulation to seventeen (17) points in the hard and soft palate in accordance with an illustrative embodiment of the invention disclosed herein.
Figure 7:
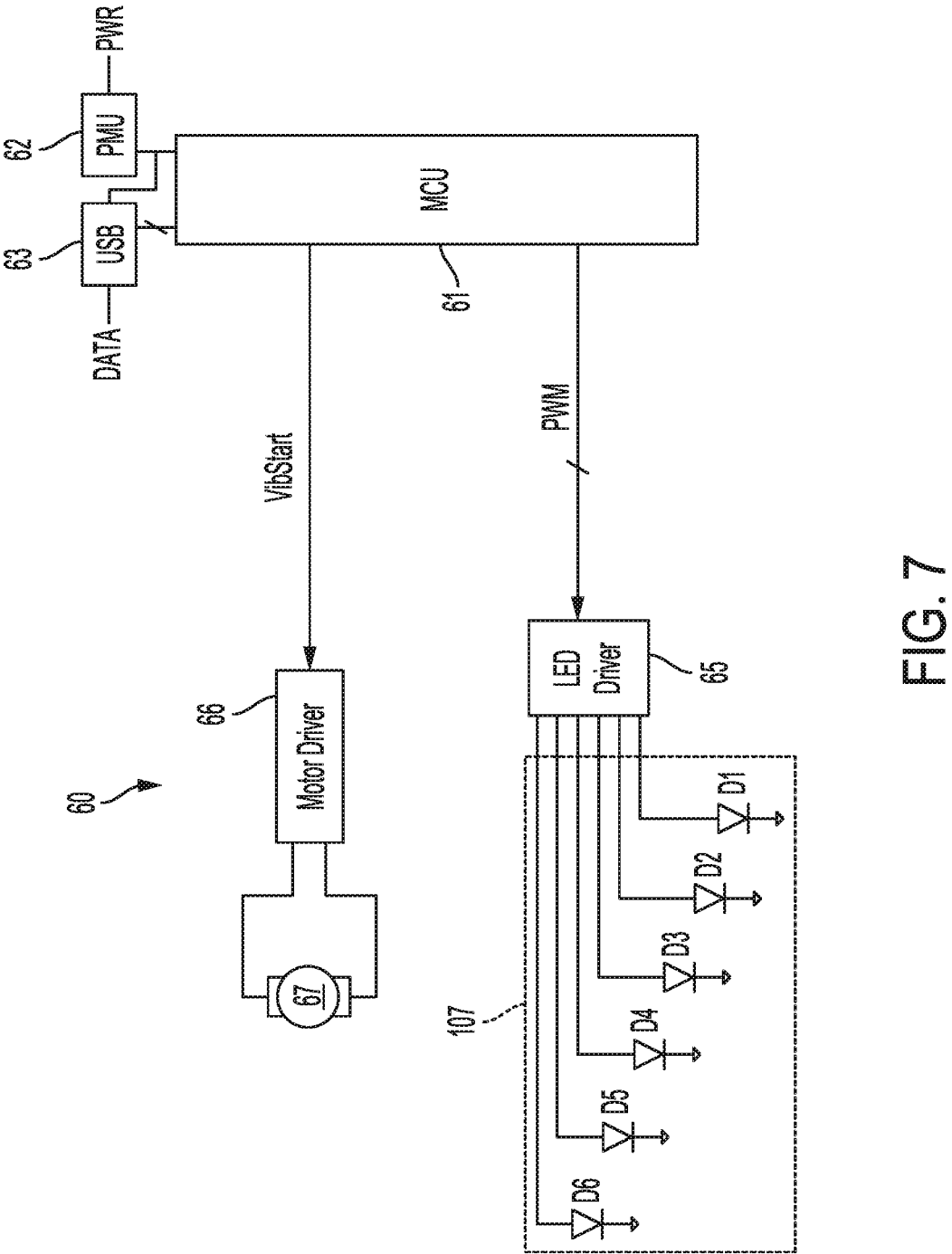
FIG. 7 is an electrical schematic of an example of an intraoral device in accordance with an illustrative embodiment of the invention disclosed herein.

The system and method detailed herein aims to enhance glymphatic and lymphatic flow within the CNS through the application of photobiomodulation, which is achieved using a transcranial vasopneumatic device 11 (as depicted in FIGS. 4 and 5) and a 670 nm LED Near-Infrared (NIR) intraoral device 60 (as illustrated in FIGS. 6 and 7). This system is further augmented by the inclusion of vibration stimulation targeting 17 specific points identified within the hard and soft palates of each individual patient.

The transcranial device 11, depicted in FIGS. 4 and 5, features a five-cell sequential vasopneumatic compression garment 1, designed for application on the head, neck, and face. To ensure comfort and suitability, the garment 1 is produced in a range of sizes to accommodate varying head and neck circumferences of individual users.

The garment 1 is outfitted with outlets that are fluidly connected to multiple air tubes 3. These tubes, in turn, are fluidly linked to an air tube bulkhead connector or manifold 4, mechanically attached to a housing 6. The manifold 4 is fluidly connected to a solenoid valve assembly 5 housed within the housing 6. The solenoid valve assembly 5 operates under control signals SolCtrl generated by a solenoid driver 58. The solenoid valve assembly 5 is fluidly linked to an air pump 57 (such as a brushless DC motor pump) operated by a motor driver 56. Both these components are situated within the housing 6.

Further detailing these connections: an air supply line 3a fluidly links the air pump 57 to the solenoid valve assembly 5, facilitating air flow from the pump 57 to the solenoid valve assembly 5. A return air supply line 3b fluidly connects the solenoid valve assembly 5 to the air pump 57. A pressure supply line 3c fluidly links the solenoid valve assembly 5 to an air pressure sensor 59 located within the housing 6. This sensor is vital for detecting the air pressure within the manifold 4. Together, these components orchestrate the vasopneumatic compression on the user.

The garment 1 also integrates an array of 810 nm pulsed NIR LEDs 2. These LEDs serve as the primary source of photobiomodulation and are controlled by an LED driver 55.

Within the housing 6 of the transcranial device 11, there is a printed circuit board (PCB) assembly 7. This is powered by a power management unit (PMU) 52, which receives power from a suitable source, such as a lithium-ion battery. The PCB assembly 7 houses a microcontroller 51, which functions as a Human-Machine Interface (HMI) controller. The microcontroller 51 features a USB interface, allowing data transmission via a USB port 53 with an external device. This interface provides a path for programming the microcontroller 51 or collecting data from it.

The transcranial device 11 also includes a touch screen 9, which is mounted on a support or holder 8 on the housing 6, and shielded by a touch screen cover 10 (typically transparent glass). The touch screen 9 is electrically connected to the microcontroller 51 and, under the control of the microcontroller 51, displays operational options to the user and accepts input commands.

Upon receiving user input via the touch screen 9, the microcontroller 51 generates a pneumatic control signal (PneuCtrl). This PneuCtrl instructs the solenoid driver 58 to generate the appropriate solenoid control signals (SolCtrl). It also produces a pump start signal (PumpStart) that directs the motor driver 56 to operate the air pump 57 suitably, executing vasopneumatic compression on the user.

Simultaneously, the microcontroller 51 generates a pulse width modulation (PWM) signal for the LED driver 55. This signal instructs the LED driver 55 to drive the NIR LEDs 2, resulting in the delivery of suitable red light pulsing for the photobiomodulation therapy applied to the user. This integrated functionality helps the transcranial device 11 attempt to provide a comprehensive and coordinated treatment, with the aim of addressing the cognitive impairment in Alzheimer's disease patients.

Referring now to FIGS. 6 and 7, the intraoral device 60, designed for stimulating glymphatic decongestion, incorporates a molded mouthpiece assembly 105, which is securely attached to upper 101 and lower 103 external assembly covers. The mouthpiece assembly 105 is engineered to adapt to a broad spectrum of variations in individuals' hard palate structures. The design of the intraoral device 60 aims to align seventeen stimulation pressure points located in the hard palate accurately against the stimulation face of the mouthpiece.

Nestled within the mouthpiece assembly 105 is a printed circuit board (PCB) 109, which is affixed to a device holder 106. The PCB 109 accommodates a linear vibration motor 67 and a series of 670 nm visible red and Near-Infrared (NIR) LEDs 107. Also situated on the PCB 109 are a motor driver 66, which controls the linear vibration motor 67 in response to a vibration start signal (VibStart), and an LED driver 65, which drives the LEDs 107 according to a received pulse width modulation (PWM) signal. This PWM signal instructs the LED driver 65 to activate the LEDs 107, resulting in the delivery of appropriate red light pulsing for the photobiomodulation therapy administered to the user.

A power management unit (PMU) 62 is also mounted to the PCB 109. It serves to regulate the power supply from the battery to the PCBs 109 and 102.

The device holder 106 extends within the upper 101 and lower 103 external assembly covers. A rechargeable battery 104, for instance, a lithium-ion battery, is positioned within the lower 103 external assembly cover. Simultaneously, a PCB 102 is held by the device holder 106 within the upper 101 external assembly cover. The PCB 102 supports a microcontroller 61, which generates the PWM and VibStart signals.

A USB interface 63 is also mounted on the PCB 102. This interface provides a conduit for data transmission, enabling programming of the microcontroller 61 or data extraction from it.

The inventive system and method will be employed to remove amyloid beta and hyperphosphorylated tau from the brains of individuals over age 65 with mild-to-moderate cognitive impairment, evidenced by baseline blood work, using blood testing for hyperphosphorylated tau, amyloid beta-40, (Aβ40, Aβ42), apolipoprotein E prototype, Amyloid Probability Score (APS, calculated from plasma Aβ42/40 ratios), and participant age. Daily treatments of vibration and photobiomodulation from the intraoral device are combined with transcranial vasopneumatic sequential pressure from the transcranial device 11 to stimulate the removal of Aβ and tau proteins from the CNS via the glymphatic and lymphatic networks. The inventive system and method can be coupled with SLUMS scores of <27 (SLUMS is scored 27-30 with high school education as normal, 21-26, mild neurocognitive disorder, and 0-20 indicating dementia) at baseline, 90 days, and 180 days.

The inventive treatment modality combines transcranial 11 and intraoral 60 devices to remove toxins from the CNS. As a basic example of treatment utilizing the devices, once daily, the patient dons the transcranial device 11 and turns the device on to deliver a sequential preset compression to the head/neck/face and a pulsed light photobiomodulation for a predetermined amount of time (e.g., 30-minute treatment setting). The patient also inserts the intraoral device 60 into their mouth and turns it on to deliver vibration stimulation and photobiomodulation to the hard and soft palates of the user's mouth. These sequential modalities decrease Aβ and Tau proteins and increase cognition for AD patients.

A more detailed treatment is as follows. Treatment is administered once daily, for a duration of 30 minutes per session. The treatment is two-pronged, employing both the transcranial device 11 and the intraoral device 60.

The user begins with the transcranial device 11. Once the device 11 is properly positioned on the user's head, neck, and face, the device 11 is activated. Upon activation, the device 11 delivers a sequence of preset millimeter of mercury (mmHg) compression to the head, neck, and face. This process is accompanied by pulsed light photobiomodulation, all within the span of the 30-minute treatment period. It's noteworthy that the mmHg in the first chamber, also identified as the "superior channel," is adjustable, and this adjustment decreases by 1 mmHg sequentially across the chambers, from superior to inferior.

As part of the process, the head garment 1 is applied as follows: The head garment 1 is unfolded such that its head strap is facing upwards. The garment 1 is placed around the back of the user's head, aligning the top of the garment 1 so its forehead strap runs across the crown of the head. The forehead strap is then pulled through the plastic loop and tightened by pulling on the strap. It is subsequently secured by attaching the hook fastener of the forehead strap to the head strap. The nose piece is then molded across the bridge of the user's nose, and the free hook fasteners are attached to the side of the head garment to ensure good contact with the user's cheeks. The garment is adjusted as necessary so that the user's vision is not obstructed. The right inner chin strap is adjusted to fit snugly under the user's chin, followed by the left outer chin strap being overlapped over the right inner chin strap and secured with the hook fastener. The garment is designed to be worn without impeding the user's vision, breathing, or swallowing.

Following the application of the transcranial device 11, the user then inserts the intraoral device 60 into their mouth and activates it. This can be performed simultaneously with the transcranial device treatment. The intraoral device 60 delivers vibration stimulation and photobiomodulation to the hard and soft palate of the user.

This dual treatment may effectively encourage glymphatic decongestion and lymphatic flow within the CNS. Indeed, the intraoral device 60 plays a helpful role in the decongestion of hyperphosphorylated tau and amyloid proteins and toxins from the brain. As explained, the device 60 utilizes vibration and photobiomodulation to stimulate seventeen specific points on the hard and soft palate. This activity propels brain hyperphosphorylated tau and amyloid proteins and toxins towards the superficial lymphatic pathway, facilitated by cranial nerves. These actions contribute to the maintenance of cerebrospinal fluid homeostasis, consequently preventing the buildup of harmful hyperphosphorylated tau and amyloid peptides, which are often implicated in the cognitive decline associated with neurodegenerative disorders.

The mechanism underlying this process involves the glymphatic network, which serves as the primary waste clearance system for proteins and metabolic byproducts in the brain. This network communicates with the authentic lymphatic network associated with the dura covering of the brain, as well as cranial nerves and large vessels at the exits of the skull. The Virchow-Robin Spaces and the Arachnoidal Septi, located along the olfactory and optical nerves, further facilitate the transportation of intracranial lymphatic load towards the subclavian lymph nodes through cervical lymph pathways.

Complementing the intraoral device 60, the transcranial device 11 applies vasopneumatic compression and Photobiomodulation to stimulate cervical and transcranial lymphatic flow. This activity routes lymphatic fluid towards the subclavian lymphatic pathway, thus clearing lymphatic congestion effectively and efficiently. The process helps maintain the homeostasis of protein and lymph, ensuring toxins and proteins are removed from perivascular spaces, and supporting overall brain health.

Together, the intraoral 60 and transcranial 11 devices function synergistically to enhance the removal of toxins, including hyperphosphorylated tau and amyloid beta, from the central nervous system (CNS). The stimulation of glymphatic and transcranial flow may enhance protein clearance from the CNS, thereby benefitting the functional daily outcomes of individuals, especially those suffering from neurodegenerative conditions.

The effectiveness of these devices can be evaluated by comparing baseline blood work and follow-up measures after a set treatment period. For instance, blood tests for hyperphosphorylated tau, amyloid beta-40, (Aβ40, Aβ42), Apolipoprotein E prototype, and the Amyloid Probability Score (APS, calculated from plasma Aβ42/40 ratios) can be used to track the removal of Aβ from the CNS.

While this novel treatment strategy has been detailed in the context of mitigating cognitive impairment due to Alzheimer's disease, those of skill in the art will appreciate the potential applicability of the system and method to a broader spectrum of brain disorders. The transcranial device 11 and the intraoral device 60 are specifically designed to stimulate the glymphatic system and facilitate the clearance of macromolecules, including amyloid-beta (Aβ) and tau proteins, from the central nervous system (CNS). As these proteins are implicated in various neurodegenerative conditions beyond Alzheimer's disease, the use of this treatment regimen can be extended to these other brain disorders as well.

Indeed, many neurological conditions may be characterized by the accumulation of abnormal proteins in the CNS. For instance, Parkinson's disease may involve the build-up of alpha-synuclein protein in the brain, while Huntington's disease may result from an excess of the Huntingtin protein. Similarly, Amyotrophic lateral sclerosis (ALS) and Fronto-temporal dementia (FTD) may be associated with the accumulation of TAR DNA-binding protein 43 (TDP-43).

In such conditions, there is a shared underlying theme of protein accumulation and impaired clearance, leading to cellular dysfunction and, eventually, neurological symptoms. By enhancing glymphatic and lymphatic flow within the CNS through the combined action of the transcranial device 11 and the intraoral device 60, it may be possible to increase the clearance of these proteins, potentially alleviating symptoms and slowing disease progression.

Therefore, the use of this innovative treatment strategy is not restricted to the treatment of Alzheimer's disease. Its potential extends to any neurological condition where the build-up of abnormal proteins contributes to disease pathology. It is a universal therapeutic approach that may play a significant role in combating a range of debilitating brain disorders associated with protein accumulation in the CNS.

If the specification or claims refer to "an additional" element, that does not preclude there being more than one of the additional elements.

It is to be understood that where the specification states that a component, feature, structure, or characteristic "may", "might", "can" or "could" be included, that particular component, feature, structure, or characteristic is not required to be included.

The description of the invention is intended to be read in connection with the accompanying drawings, which are to be considered part of the entire written description of this invention. In the description, relative terms such as "front," "rear," "lower," "upper," "horizontal," "vertical," "inward," "outward," "up," "down," "top" and "bottom" as well as derivatives thereof (e.g., "horizontally," "downwardly," "upwardly" etc.) should be construed to refer to the orientation as then described or as shown in the drawings under discussion. These relative terms are for convenience of description and do not require that the device be constructed or the method to be operated in a particular orientation. Terms, such as "connected," "connecting," "attached," "attaching," "join" and "joining" are used interchangeably and refer to one structure or surface being secured to another structure or surface or integrally fabricated in one piece.

For purposes of the instant disclosure, the term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)–(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

Thus, the invention is well adapted to carry out the objects and attain the ends and advantages mentioned above as well as those inherent therein. While the inventive concept has been described and illustrated herein by reference to certain illustrative embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. A method of treating neurodegenerative diseases involving accumulation of abnormal proteins in the central nervous system (CNS) of a user, the method comprising:
    utilizing an intraoral device to apply photobiomodulation and vibration to specific points on hard and soft palates of the user to stimulate the user's glymphatic system and decongest tau and amyloid proteins and toxins; and
    simultaneously with the utilization of the intraoral device, applying a transcranial device comprising a head and neck garment to exert vasopneumatic compression and photobiomodulation on the user's head and neck to stimulate the user's lymphatic system and enhance the flow of lymphatic fluid toward the subclavian lymphatic pathway.

2. The method of claim 1, further comprising repeating the utilization of the intraoral device and the application of the transcranial device on a daily basis to enhance clearance of abnormal proteins from the CNS and thereby alleviate symptoms of the neurodegenerative disease.

3. The method of claim 1, wherein the intraoral device is utilized to apply vibration and photobiomodulation to a plurality of specific points on the hard and soft palate.

4. The method of claim 1, wherein the intraoral device is utilized to apply vibration and photobiomodulation to seventeen specific points on the hard and soft palate.

5. The method of claim 1, wherein the transcranial device is utilized to apply the vasopneumatic compression and photobiomodulation to stimulate cervical and transcranial lymphatic flow.

6. The method of claim 1, wherein the abnormal proteins include hyperphosphorylated tau and amyloid-beta proteins.

7. The method of claim 1, wherein the neurodegenerative disease is selected from the group consisting of Alzheimer's disease, Parkinson's disease, Huntington's disease, and Amyotrophic lateral sclerosis (ALS).

8. A system for treating neurodegenerative diseases involving accumulation of abnormal proteins in the central nervous system (CNS), the system comprising:

an intraoral device designed to fit hard and soft palates of a user, the intraoral device comprises a vibration mechanism and a set of photobiomodulation elements and is configured to apply photobiomodulation and vibration to specific points on the hard and soft palate of the user to stimulate the user's glymphatic system and decongest tau and amyloid proteins and toxins; and a transcranial device comprising a head and neck garment having integrated vasopneumatic compression elements and photobiomodulation elements, the transcranial device configured to exert vasopneumatic compression and photobiomodulation on the user's head and neck to stimulate the user's lymphatic system and enhance the flow of lymphatic fluid towards the user's subclavian lymphatic pathway.

9. The system of claim 8, wherein the vibration mechanism of the intraoral device includes a motor driver that drives a linear vibration motor, and wherein the set of photobiomodulation elements of the intraoral device includes an LED driver that drives a plurality of visible red and NIR LEDs.

10. The system of claim 8, wherein the head and neck garment is configured to exert vasopneumatic compression and photobiomodulation on the user's head and neck region, and wherein the transcranial device further includes a control unit that adjusts the vasopneumatic compression and photobiomodulation intensity in response to pre-set treatment protocols.

11. The system of claim 8, wherein the vibration mechanism and the set of photobiomodulation elements of the intraoral device are configured to apply vibration and photobiomodulation to a plurality of specific points on the hard and soft palate.

12. The system of claim 8, wherein the vibration mechanism and the set of photobiomodulation elements of the intraoral device are configured to apply vibration and photobiomodulation to seventeen specific points on the hard and soft palate.

13. The system of claim 8, wherein the abnormal proteins include tau and amyloid-beta proteins.

* * * * *